United States Patent [19]

Christensen

[11] Patent Number: Plant 6,861

[45] Date of Patent: Jun. 20, 1989

[54] HYBRID TEA ROSE PLANT CV. AROGREWOD

[75] Inventor: Jack E. Christensen, Ontario, Calif.

[73] Assignee: Armstrong Garden Centers, Inc., Monrovia, Calif.

[21] Appl. No.: 132,576

[22] Filed: Dec. 14, 1987

[51] Int. Cl.[4] ..... A01H 5/00

[52] U.S. Cl. ..... Plt./11

[58] Field of Search ..... Plt./11, 18

*Primary Examiner*—Robert E. Bagwill

*Attorney, Agent, or Firm*—William H. Elliott, Jr.

[57] ABSTRACT

This invention relates to a new and distinct variety of hybrid tea rose plant cv. Arogrewod particularly suited for garden decoration, and characterized by its classically shaped flowers of light lavender on the inside surface of the petals and creamy white on the outside surface of the petals.

1 Drawing Sheet

1

The present invention relates to a new and distinct variety (cv. Arogrewod) of rose plant of the hybrid tea class. The plant is a bushy, outdoor seedling of average height, cultivated for garden decoration. Its hardiness is, as yet, untested. It was first originated by Jack E. Christensen in Ontario, Calif., U.S.A. under conditions of careful control and observation, and has as its seed parent, an unnamed hybrid tea rose seedling selected from a cross between the hybrid tea rose Ivory Tower (U.S. Plant. Pat. No. 4,658) and the floribunda rose Angel Face (U.S. Plant Pat. No. 2,792) and, as its pollen parent, the hybrid tea rose, Paradise (U.S. Plant Pat. No. 4,552).

The new rose cv. Arogrewod is particularly distinguishable from other commercialized rose cultivars by the following combination of characteristics: its vigorous growing plants of average height having a moderate number of strong stems; its classically shaped flowers; its flower color comprising a light lavender color on the inside surface of the petals and a creamy white on the outside petal surface; and its moderate fruity fragrance.

Arogrewod holds its distinguishing characteristics through succeeding propagations by budding.

The new variety cv. Arogrewod may be distinguished from its seed parent by the following combination of characteristics: Arogrewod is a more vigorous growing plant than its seed parent. Its flowers are more high-centered and larger in diameter than the flowers of its seed parent. Whereas the flower color of Arogrewod is a creamy white on the outside surface of the petals and a light lavender on the inside surface of the petals, the flower color of the seed parent is a blend of lavender and white on the outside surface of the petals and a lighter lavender on the inside surface of the petals. The flower fragrance of the seed parent is strong and citrus-like whereas the flower fragrance of Arogrewod is moderate and fruity.

The new variety may be distinguished from its pollen parent, Paradise, by the following combination of characteristics: Whereas the flower color of Paradise is a mauve with red edges, the flower color of Arogrewod is a light lavender on the inside surface of its petals and a creamy white on the outside surface of its petals. The flower fragrance of Arogrewod is moderate and fruity whereas the flower fragrance of Paradise is less pronounced.

2

The accompanying drawing illustrates the new variety in color as grown in Somis, Calif., and shows the flowering thereof from bud to full bloom.

The descriptive matter which follows pertains to roses of the new variety grown outdoors in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety usually bears a single flower per a stem, sometimes two to three to a stem in irregular clusters. Flower stems are strong and of average length to long for the class. Outdoors, the plant blooms abundantly and continuously during the growing season. Blooms have a moderate fruity fragrance.

BUD

The peduncle is of average length for the class, of average to heavy caliper, strong and erect. The peduncle is moderately smooth with some stipitate glands. Bud color is near Green 139C.

Before the calyx breaks, the bud is large in size for the class, of average length, long, pointed and ovoid in form with a conspicuous neck. There are stipitate glands and a glandular bloom on the surface of the bud. The bud lacks foliaceous parts extending beyond the tip of the bud.

As the calyx breaks, those areas of the outer petals exposed to sunlight are near Greyed-Purple 186A in color; areas of the outer petals shielded from sunlight by the sepals are near Green-White 157D in color.

The inner surface of the sepals is lined with a fine wooly tomentum. Sepal margins are lined with stipitate glands, gland-tipped cilia and hairs.

As the first petal opens, buds are average to large in size for the class, average to long in length, pointed and urn-shaped in form. The color of the outside surface of the bud petals is near Green-White 157D at the base of the bud, blushing to a light lavender at the top of the bud, near Purple 75D. Areas of the outside bud petal exposed to sunlight darken further to a richer lavender, near Greyed-Purple 186A. The inside surface of the bud petals is a light lavender color, near Purple 75D.

The bud opens up well and is not prevented from opening by cold, hot, wet or dry weather.

BLOOM

The size of the bloom when fully open is average to large for the class, about 4½ to 5 inches in diameter. Petalage is very double, averaging from about 30 to about 34 petals arranged regularly, plus 1 to 2 petaloids.

Blooms at one half open are very high centered in form, with petals moderately cupped. Petal edges are somewhat reflexed outward.

When fully open, the blooms are moderately cupped with loosely cupped petals, the edges of which are slightly reflexed outward.

The petals are of heavy substance, thick and slightly shiny to satiny on the inside and outside surfaces. Outside petals are nearly round to broadly obovate in shape, with rounded apices usually bearing 0 to 1 notch. Intermediate petals are broadly obovate in shape with rounded apices bearing zero to one notch. Inside petals are nearly round to broadly obovate, with rounded apices usually bearing zero to one notch.

Petal colors may be modified by being margined, washed or tinted with other colors.

The following paragraph describes the color values observed in a newly opened flower from a plant of the new variety grown outdoors in Somis, Calif. in November of 1987.

The color of the outside surface of the outside petals is a light yellow on the lower ¼ of the petal, near Yellow 1D, and a light lavender, near Red-Purple 62C, on the upper three quarters of the petal. The inside surface of the outside petal is a light yellow, near Green-Yellow 1B at the petal base; near Red-Purple 62D in the mid-portion of the petal; and near Red-Purple 67D on the outer petal margin.

The outside surface of the intermediate petals is near Green-Yellow 1A at the petal base, blending into a creamy white, near White 155A, coloring the balance of the petal surface. The inside surface of the intermediate petals is near Green-Yellow 1A at the petal base, blending into a light lavender, near Purple 75D, coloring the balance of the petal surface. The outside surface of the inner petals is near Green-Yellow 1A at the petal base, blending into a creamy white, near White 155A, coloring the balance of the petal surface. The inside surface of the inner petal is near Green-Yellow 1A at the petal base, blending into a light lavender, near Purple 75D, coloring the balance of the petal surface.

The following paragraph describes the color values observed in a flower open for three days outdoors from a plant of the new variety in November, 1987 at Somis, Calif.

The color of the outside surface of the outside petals is a light yellow green at the petal base, near Green-Yellow 1D, blending into a light pink, near Red 56A, coloring the balance of the petal. The inside surface of the outside petal is a light yellow at the petal base, near Green-Yellow 1C, blending into a light pink, near Red 56A, in the middle portion of the petal, deepening to a light lavender, near Red-Purple 68A, over the upper portion of the petal. The color of the outside surface of the inside petal is a light yellow at the petal base, near Green-Yellow 1C, blending into a creamy white, near White 155D, coloring the balance of the petal surface. The color of the inside surface of the inside petal is a light yellow at the petal base, near Green-Yellow 1B, blending into a pale lavender, near Red 56D, coloring the balance of the petal surface.

The general color effect of the newly opened flower is a bicolor, elegant lavender on the inside surfaces of the petals and creamy white on the outside surfaces of the petals.

After being open three days, the general color effect of the flower is a very light lavender with pinkish-red margins.

Petals usually drop off cleanly and are not particularly affected by hot, cold, wet or dry weather.

Flowers grown on a bush in the garden last from 4 to 5 days in the month of September. Cut flowers from rose plants grown outdoors in Septemter last from 5 to 6 days when kept at living room temperatures.

REPRODUCTIVE ORGANS

Stamens are many in number and are arranged regularly about the pistils; a few may also be mixed with petaloids. Filaments are average in length and most have average sized anthers. Anthers open approximately all at once. Mature anthers are near Yellow-Orange 16B in color; immature anthers are near Yellow-Orange 16C in color. Pollen is produced in moderate to abundant quantities and is near Yellow-Orange 16B in color.

Pistils are many in number for the class (about 50). Styles are even, short to average in length, of average caliper, and are bunched. Stigma color is near Yellow-Orange 16D. Ovaries are all enclosed in the calyx.

Hips are of average length, globular to pear shaped in form, with an inconspicuous neck. Hips are near Orange 26A in color. Hip walls are thick and their outer surface is smooth.

Sepals are permanent, of average length and recurved. At hip maturity, the outside and inside sepal surface is a blackened brown, near Brown 200A.

Seeds are produced in average quantities, about 25–30 in number, and are small to medium in size for the class.

FOLIAGE

The compound leaves comprise 5 to 7 leaflets. Leaves are borne in normal to abundant quantities and are of average to large size for the class. Leaves are somewhat leathery and are semi-glossy. Leaflets are oval to obovate in shape, with acute apices; their bases are round and their margins are simply serrate.

The color of the upper surface of mature leaves is near Green 139A with a reddish tint near Greyed-Purple 186A. The under surface of the mature leaf is near Greyed-Green 193A with a reddish tint near Greyed-Purple 186A. The upper surface of the young leaves is near Green 138A with dark red tints, near Greyed-Purple 186A. The under surface of young leaves is near Greyed-Green 193A in color, blended with crimson red, near Greyed-Purple 186A.

The rachis is average in size. Its upper side is grooved with some stipitate glands on the edges. The underside is moderately prickly with stipitate glands.

Stipules are average in length for the class and narrow, having short points turning out at an angle of usually 45°.

Plants of the new variety are average in their resistance to mildew, rust and blackspot as compared with other cultivars now in commerce when grown under comparable conditions at Somis, Calif.

GROWTH

Plants of the new variety are tall and upright, moderately branched and bushy in habit. Plant growth is vigorous. Canes are of heavy caliper for the class. The main stems are near Yellow-Green 147C in color. They bear several large thorns which are of average length for the class and hooked downward. The thorn base is of average length and is moderately narrow. Large thorns are between near Greyed-Orange 166B and Greyed-Orange 166C in color. There are no small prickles and no hairs.

Branches are near Yellow-Green 147C in color. They bear several large thorns which are moderately short to average in length for the class. Large thorns are hooked downward and have narrow bases of average length.

Large thorns are between near Greyed-Orange 166B and Greyed-Orange 166C in color. There are no small prickles and no hairs.

New shoots are near Green 147A in color. New shoots bear few to several large thorns which are short to average in length for the class. Large thorns are hooked downward and have short narrow bases of average length. Large thorns are near Greyed-Purple 185A in color. There are no small prickles and no hairs.

I claim:

1. A new and distinct variety of hybrid tea rose plant cv. Arogrewod and the parts thereof, being particularly characterized by its vigorous growing plants of average height having a moderate number of strong stems; its classically shaped flowers; its flower color comprising a light lavender color on the inside surface of the petals and a creamy white on the outside petal surface; and its moderate fruity fragrance, substantially as described and illustrated herein.

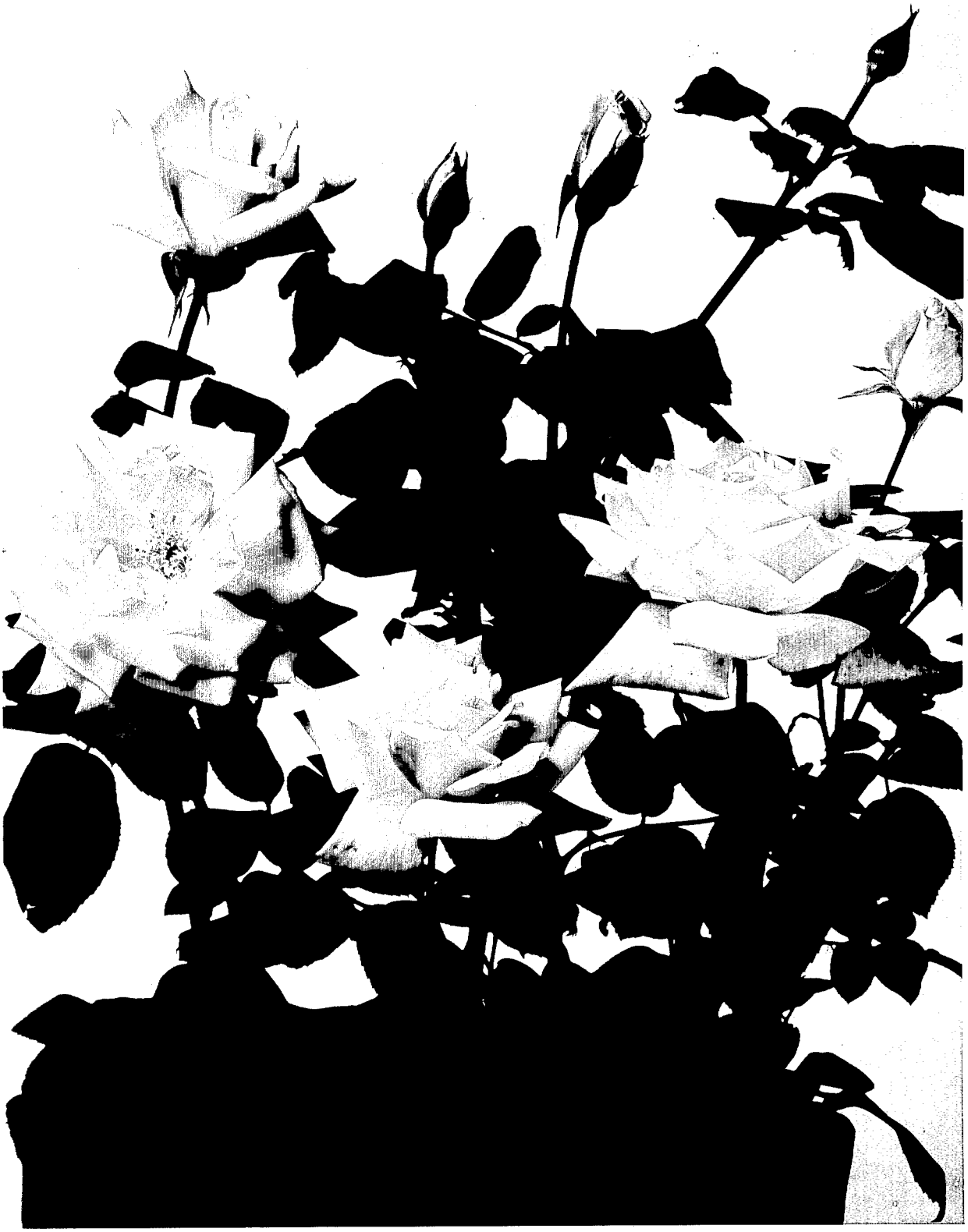

* * * * *